United States Patent
Eder

(10) Patent No.: US 9,702,825 B2
(45) Date of Patent: Jul. 11, 2017

(54) ASSEMBLY FOR ANALYZING A LIGHT PATTERN CAUSED BY REFRACTION AND REFLECTION AT A PRECIOUS STONE

(71) Applicant: D. Swarovski KG, Wattens (AT)

(72) Inventor: Karlheinz Eder, Buch in Tirol (AT)

(73) Assignee: D. SWAROVSKI KG, Wattens (AT)

( * ) Notice: Subject to any disclaimer, the term of this patent is extended or adjusted under 35 U.S.C. 154(b) by 0 days.

(21) Appl. No.: 15/040,338

(22) Filed: Feb. 10, 2016

(65) Prior Publication Data

US 2016/0161421 A1    Jun. 9, 2016

Related U.S. Application Data

(63) Continuation of application No. PCT/AT2014/000134, filed on Jun. 30, 2014.

(30) Foreign Application Priority Data

Aug. 27, 2013  (AT) .................... A 659/2013

(51) Int. Cl.
| | | |
|---|---|---|
| *G01N 21/00* | (2006.01) | |
| *G01N 21/87* | (2006.01) | |
| G01N 21/47 | (2006.01) | |
| G01N 21/55 | (2014.01) | |

(52) U.S. Cl.
CPC .......... *G01N 21/87* (2013.01); *G01N 21/4788* (2013.01); *G01N 21/55* (2013.01); *G01N 2201/061* (2013.01); *G01N 2201/0634* (2013.01)

(58) Field of Classification Search
CPC .... G01N 21/87; G01N 21/4788; G01N 21/55; G01N 2201/061; G01N 2201/0634
USPC .......................................................... 356/30
See application file for complete search history.

(56) References Cited

U.S. PATENT DOCUMENTS

| | | | |
|---|---|---|---|
| 3,708,217 A * | 1/1973 | McMahon | ........... G02B 5/0252 |
| | | | 359/15 |
| 3,867,032 A | 2/1975 | Bruck | |
| 3,947,120 A | 3/1976 | Bar-Issac et al. | |
| 4,397,556 A | 8/1983 | Muller | |
| 4,900,147 A | 2/1990 | Bowley et al. | |

(Continued)

FOREIGN PATENT DOCUMENTS

| | | |
|---|---|---|
| AT | 344 419 | 7/1978 |
| DE | 24 50 194 | 5/1975 |

(Continued)

OTHER PUBLICATIONS

International Search Report issued Oct. 31, 2014 in International (PCT) Application No. PCT/AT2014/000134.

*Primary Examiner* — Hina F Ayub

(74) *Attorney, Agent, or Firm* — Wenderoth, Lind & Ponack, L.L.P.

(57) ABSTRACT

An assembly for analyzing a light pattern caused by refraction and reflection at a precious stone, comprising a light source for illuminating the precious stone, a retaining device for retaining the precious stone, a diffusing screen for imaging the light pattern, and a camera for recording the light pattern imaged on the diffusing screen. The assembly comprises a semi-transmitting optical element for deflecting, in a direction of the precious stone, light emitted by the light source and transmitting the light refracted and reflected at the precious stone.

19 Claims, 2 Drawing Sheets

(56) References Cited

U.S. PATENT DOCUMENTS

| | | | |
|---|---|---|---|
| 5,196,966 A | 3/1993 | Yamashita | |
| 5,536,943 A | 7/1996 | Smith et al. | |
| 5,828,405 A | 10/1998 | Vanier et al. | |
| 6,515,738 B1 * | 2/2003 | Barres | G01N 21/87 356/30 |
| 8,212,871 B2 | 7/2012 | Tonogai et al. | |
| 2001/0023925 A1 | 9/2001 | Smith | |
| 2004/0072137 A1 * | 4/2004 | Lapa | G09B 5/02 434/386 |
| 2009/0102939 A1 * | 4/2009 | Ahuja | G03B 19/00 348/222.1 |
| 2010/0110180 A1 | 5/2010 | Tonogai et al. | |
| 2010/0157078 A1 * | 6/2010 | Atanassov | G06T 5/007 348/222.1 |
| 2011/0176563 A1 * | 7/2011 | Friel | C30B 25/02 372/3 |
| 2011/0299063 A1 * | 12/2011 | Ninomiya | G01N 21/251 356/31 |
| 2013/0208282 A1 | 8/2013 | Nizienko | |
| 2016/0178530 A1 * | 6/2016 | Davies | G01N 21/87 209/578 |

FOREIGN PATENT DOCUMENTS

| | | |
|---|---|---|
| DE | 29 35 812 | 3/1981 |
| EP | 0 464 824 | 1/1992 |
| EP | 2 554 978 | 2/2013 |
| GB | 2 267 147 | 11/1993 |
| JP | 53-78855 | 7/1978 |
| JP | 2006-145280 | 6/2006 |
| JP | 2010-134915 | 6/2010 |
| WO | 97/04303 | 2/1997 |

\* cited by examiner

ASSEMBLY FOR ANALYZING A LIGHT PATTERN CAUSED BY REFRACTION AND REFLECTION AT A PRECIOUS STONE

BACKGROUND OF THE INVENTION

1. Field of the Invention

The invention concerns an assembly for analyzing a light pattern caused by refraction and reflection at a precious stone, comprising a light source for illuminating the precious stone, a holding device for holding the precious stone, a diffusing screen for imaging the light pattern (in particular, a flat diffusing screen), and a camera for recording the light pattern imaged on the diffusing screen. The invention further concerns a method of analyzing a light pattern caused by refraction and reflection at a precious stone by means of the assembly according to the invention.

2. Description of Related Art

An assembly having the specified components is known, for example, from U.S. Pat. No. 5,828,405. A disadvantage with that assembly in the state of the art is that illumination of the diamond to be investigated is effected by way of an opening in the diffusing screen. The result of this is that the part of the light pattern which would be imaged in the region of that opening on the diffusing screen is lost. In addition, only a small part of the diamond can be illuminated with the illumination arrangement disclosed in U.S. Pat. No. 5,828,405. In that way, also there is a loss of information about the diamond.

Also finally there is the further disadvantage that, by virtue of the geometry of the illumination arrangement, it is necessary for the camera for recording the light pattern imaged on the diffusing screen to be arranged at an angle relative to the screen and, on the other hand, to be positioned relatively close to the diffusing screen. The latter requires the use of an extreme fisheye objective. Overall, the arrangement of the camera in relation to the diffusing screen in U.S. Pat. No. 5,828,405 results in severe perspective distortions of the recorded light pattern. Theoretically, it would admittedly be possible to increase the distance of the camera relative to the diffusing screen so that the camera is disposed, for example, at the height of the precious stone or even behind the precious stone, but then the free view onto the diffusing screen would be restricted by parts of the illumination arrangement or the precious stone itself, which again would lead to information loss.

For the sake of completeness, however, it should also be noted that the aim in U.S. Pat. No. 5,828,405 is to record a characteristic "fingerprint" of a precious stone and to compare it to a fingerprint stored in a database in order to be able to identify the precious stone in the event of theft. As long as the image of the precious stone is always recorded with the same apparatus, information losses and perspective distortions do not play any part.

SUMMARY OF THE INVENTION

In contrast thereto, the assembly of the present invention is used for analysis of a light pattern caused by refraction and reflection at a precious stone. This, for example, involves analyzing the quality of a precious stone, which is influenced, for example, by parameters like geometry or polish. Against the background of that aim, the above-mentioned disadvantages do in fact play a definite part.

It should be noted that the present assembly or the present method in principle can be used for the analysis of all kinds and shapes of precious stones. In particular, it is also possible to analyze natural or synthetically produced precious stones and gemstones like, for example, zirconia or precious stones made from glass (glass stones).

The object of the present invention is to avoid the disadvantages known from the state of the art and to provide an improved assembly for analyzing a light pattern caused by refraction and reflection at a precious stone and an improved method for the same, in which the assembly according to the invention is used.

That object is attained by the features described herein.

One of the core concepts of the present invention, therefore, is that the assembly includes a semi-transmitting optical element for deflection of the light from the light source in the direction of the precious stone and transmission of the light refracted and reflected at the precious stone, wherein the semi-transmitting optical element is, for example, a semi-transmitting mirror or a glass plate.

One of the essential differences over the state of the art, therefore, is that the light coupling-in effect is implemented by way of a semi-transmitting optical element. In that way, it is possible to more flexibly arrange the elements of the assembly and avoid the disadvantages known from the state of the art.

By way of example, the holding device for holding the precious stone and the light source for illuminating the precious stone can be arranged on the same side of the diffusing screen. That has the advantage that a hole does not have to be provided in the diffusing screen for illumination of the precious stone. At the same time, space is also provided for a substantially perpendicular arrangement of the camera for recording the light pattern imaged on the diffusing screen, relative to the diffusing screen. For that purpose, it can be provided that the camera is arranged on the side of the diffusing screen that is opposite to the holding device, and/or the diffusing screen is a transmission screen. By virtue of such an arrangement of the camera in relation to the diffusing screen, it is possible for the spacing of the camera relative to the diffusing screen to be so selected that it is possible to use objectives which result in no or only very slight perspective distortions of the imaged light pattern. In addition, it is possible to entirely avoid information losses as there is no longer any need to arrange between the camera and the diffusing screen elements which adversely affect a free view of the camera onto the diffusing screen.

The apparent disadvantage due to the use of an additional optical element in the form of a semi-transmitting optical element (any optical element is always linked to more or less severely pronounced imaging defects) is therefore more than compensated by a series of advantages.

In an advantageous configuration of the assembly according to the invention, the holding device is arranged at a spacing of between 10 cm and 50 cm, preferably at a spacing of about 30 cm, from the diffusing screen.

In addition, it has proven to be advantageous if the camera includes a CCD chip and/or the light source is a light-emitting diode (LED) light source.

The light emitted from the light source is preferably unpolarized, and/or has a beam diameter of between 5 mm and 15 mm, preferably a beam diameter of about 10 mm, and/or is collimated, and/or has a half-angle divergence of between 0.1° and 0.4°, preferably a half-angle divergence of about 0.25°, and/or has a spectrum with a plurality of different wavelengths from the range of visible light. The latter manifests itself in that the precious stone is illuminated substantially with white light which, in part, is broken down into its spectral colors by refraction at the precious stone so that the light pattern imaged on the diffusing screen includes, in part, colored light reflections.

Preferably, it is also provided that the assembly according to the invention includes an evaluation unit, preferably a computer, for evaluation of the light pattern recorded by the camera, and/or at least the light source, the holding device, the diffusing screen, the camera and the semi-transmitting optical element are arranged in an apparatus for suppressing background light. The latter measure makes it possible to markedly improve the signal-noise ratio.

As stated in the opening part of this specification, a method of analyzing a light pattern caused by refraction and reflection at a precious stone by means of an assembly according to the invention is also provided, wherein the method includes the following steps: holding the precious stone to be analyzed in the holding device, illuminating the precious stone by means of the light source and recording the light pattern imaged on the diffusing screen by means of the camera.

In a particularly preferred embodiment of that method, it is provided that method steps 2 and 3 are repeated at least once with a differing illumination time and/or with a differing intensity and/or with a differing polarization (in the case where polarized light is used). As a further consequence, it is then more specifically possible—if evaluation of the light pattern recorded by the camera by means of the evaluation unit is included as a further method step—to produce an HDR (high dynamic range) image with an increased information content from at least two light patterns recorded with differing illumination times and/or intensities and/or polarizations.

Also finally it has proven to be desirable for the light pattern recorded by the camera to be compared to at least one light pattern stored in the evaluation unit, in which case the stored light pattern preferably involves a simulated light pattern. In that way, it is possible, for example, to detect deviations from an ideal cut of the precious stone.

BRIEF DESCRIPTION OF THE DRAWINGS

Further features and advantages of the present invention will be apparent from the Figures and the following specific description. In the Figures.

DETAILED DESCRIPTION OF THE INVENTION

Figure 1:
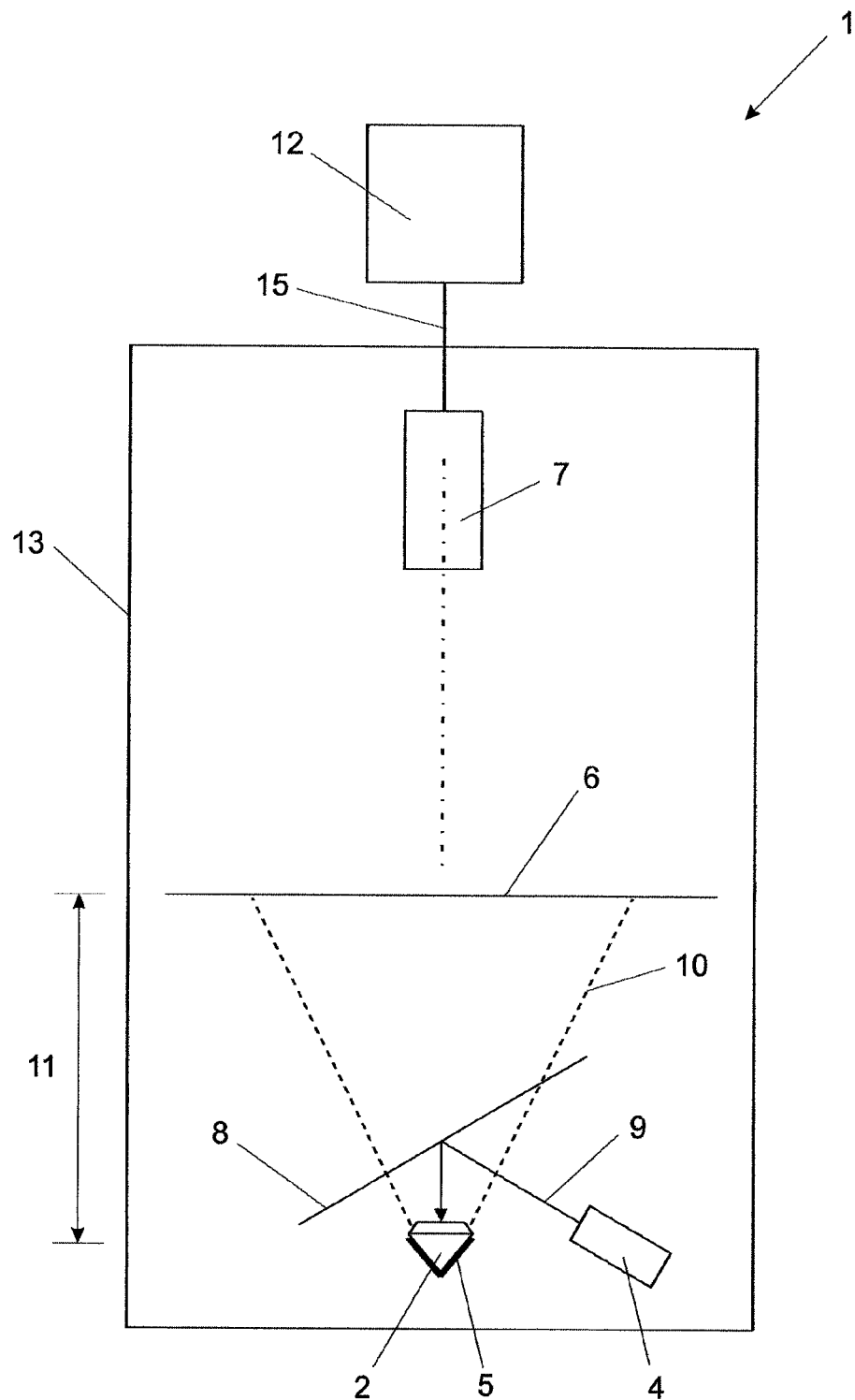
FIG. 1 shows a diagrammatic view of a preferred embodiment of the assembly.

The preferred embodiment as shown in FIG. 1 of the assembly 1 according to the invention for analyzing a light pattern caused by refraction and reflection at a precious stone includes a light source 4 for illuminating a precious stone 2 held in a holding device 5. In that case, an LED light source is used as the light source 4. The light from the light source 4—the corresponding optical axis is denoted by reference 9—is unpolarized, it is of a beam diameter of about 10 mm, it is collimated and it has a half-angle divergence of about 0.25° as well as a spectrum with a plurality of different wavelengths from the range of visible light. Most commercially usual precious stones can be completely illuminated by virtue of the magnitude of the beam diameter.

The light 9 issuing from the light source 4 is initially incident at an angle on a semi-transmitting optical element 8 in the form of a semi-transmitting mirror and is reflected at the surface, that is, towards the light source of the semi-transmitting optical element 8. More precisely, the light is deflected in the direction of the precious stone 2. In that case, a part of the light incident on the precious stone 2 is immediately reflected in the direction of the diffusing screen 6. The remaining part—which is much greater—of the light passes into the precious stone 2, is refracted there and experiences total reflections at the surfaces of the faceted precious stone 2 until finally it issues from the precious stone 2 again in the direction of the diffusing screen 6. Naturally, a part of the light also leaves the precious stone 2 in a direction away from the diffusing screen 6 and is thus "lost" in regard to the light pattern.

The refracted and reflected light 10 issuing from the precious stone 2 to be analyzed—being indicated by the broken lines—passes in a transmission mode through the semi-transmitting optical element 8 and is then incident on the diffusing screen 6 on which a diffusion image which is characteristic in accordance with the respective kind of the precious stone 2 is imaged. The spacing of the holding device 5 and thus (approximately the center) of the precious stone 2 relative to the diffusing screen 6 is about 30 cm.

As can be seen from the structure of the assembly 1 as shown in FIG. 1, the holding device 5 and the light source 4 are arranged on the same side of the diffusing screen 6.

The diffusing screen 6 is a transmission screen, that is to say the light pattern imaged on the diffusing screen 6 is also visible on the side of the diffusing screen 6, that is, away from the holding device 5. In that way, it is possible for the light pattern imaged on the diffusing screen 6 to be recorded by means of a camera 7 arranged on the side of the diffusing screen 6 that is opposite to the holding device 5. In addition, it is also possible for the camera 7 to be oriented in its longitudinal extent substantially perpendicularly to the diffusing screen 6, as indicated by the dash-dotted line. The camera 7 is a CCD camera with a corresponding CCD chip.

The light source 4, the holding device 5, the diffusing screen 6, the camera 7 and the semi-transmitting optical element 8 are arranged in an apparatus 13 for suppressing background light, the walls of the apparatus 13 having a black matte surface.

The camera 7 is connected to an evaluation unit 12 in the form of a computer by way of a suitable data line 15 which can also be of a wireless nature.

Figure 2:
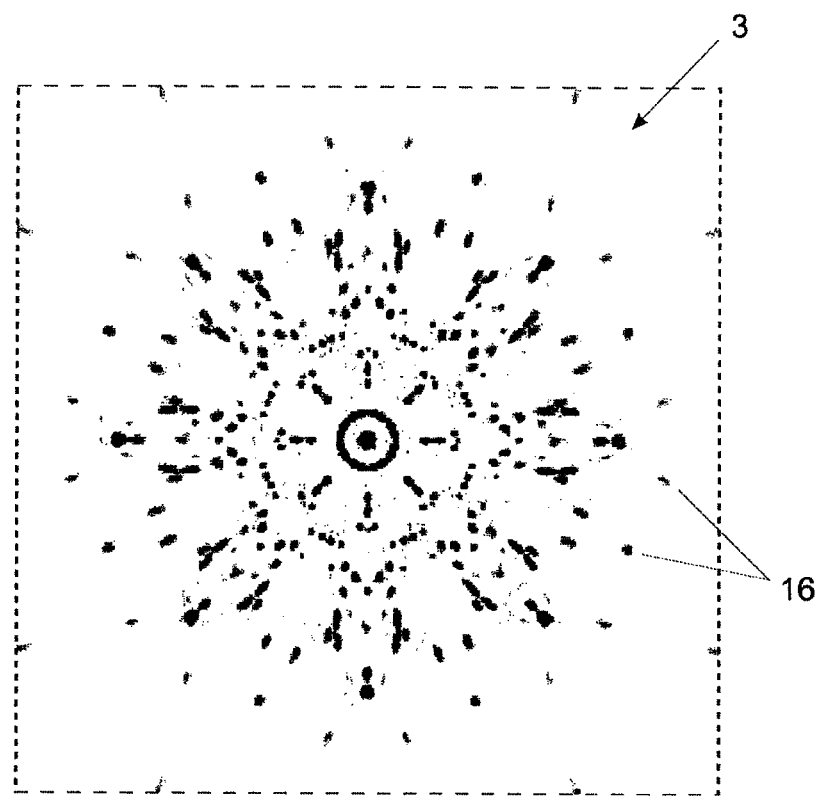
FIG. 2 shows, by way of example, a simplified diagrammatic view of a light pattern produced by refraction and reflection at a precious stone and imaged on the diffusing screen.

FIG. 2 is a black-and-white illustration by way of example illustrating a light pattern 3 produced by refraction and reflection at a precious stone and imaged on the diffusing screen. That light pattern 3 is composed of individual light flecks 16, those light flecks 16 being produced by refraction and reflection characteristically for each precious stone. It should be noted that the image shown in FIG. 2 is a false color image with inverted luminosity. The white regions are in reality black, that is to say no light reaches here, and the dark regions are those regions of the diffusing screen on which light is incident. Due to the simplified black-and-white illustration, it is also not possible to see that the light flecks 16 in part have a color pattern which is similar to the breakdown of white light by a prism. It should also be noted that the light flecks 16 can be of a differing luminosity. In the English-language literature, such a light pattern of a precious stone is frequently also referred to as its "fire".

Figure 3:
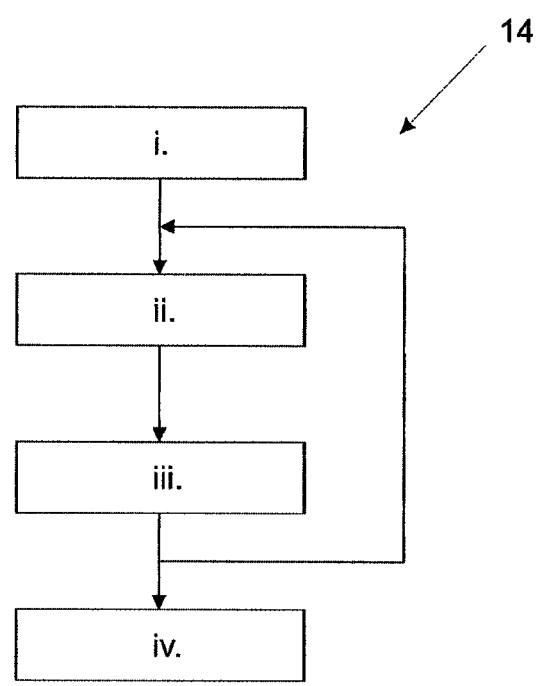
FIG. 3 shows a flow chart to diagrammatically illustrate a preferred embodiment of the method according to the invention.

FIG. 3 shows a flow chart illustrating a preferred embodiment of the method 14 according to the invention: in a first step i., a precious stone to be analyzed is held in the holding device. In a subsequent method step ii., illumination of the precious stone is effected by means of the light source. In a third method step iii., the light pattern imaged on the diffusing screen is recorded by means of the camera. Method steps ii. and iii. are then repeated with a series, for example, ten, of differing illumination times, ranging, for example, between about 60 ms and about 16000 ms, that is to say light patterns which are produced with differing illumination times are successively recorded by means of the camera.

In a further method step iv., evaluation of the light pattern recorded by the camera is effected by means of the evaluation unit. For that purpose, an HDR image is firstly produced from the light patterns recorded with differing illumination times and then compared to a light pattern which is stored in the evaluation unit and which is a simulated light pattern. On the basis of that comparison, it is possible to draw conclusions about the quality of the precious stone.

The invention claimed is:

1. An assembly for analyzing a light pattern caused by refraction and reflection at a precious stone, the assembly comprising:
   a light source for illuminating the precious stone;
   a holding device for holding the precious stone;
   a diffusing screen for imaging the light pattern;
   a camera for recording the light pattern imaged on the diffusing screen; and
   a semi-transmitting optical element for deflection of light emitted by the light source in a direction of the precious stone and transmission of light refracted and reflected at the precious stone,
   wherein the camera is arranged on a side of the diffusing screen that is opposite to the holding device, and/or is oriented substantially perpendicularly to the diffusing screen and/or the diffusing screen is a transmission screen, and
   wherein the diffusing screen is flat.

2. The assembly as set forth in claim 1, wherein the semi-transmitting optical element is a semi-transmitting mirror or a glass plate.

3. The assembly as set forth in claim 1, wherein the holding device and the light source are arranged on a same side of the diffusing screen.

4. The assembly as set forth in claim 1, wherein the holding device is arranged at a spacing of between 10 cm and 50 cm from the diffusing screen.

5. The assembly as set forth in claim 4, wherein the spacing is 30 cm from the diffusing screen.

6. The assembly as set forth in claim 1, wherein the camera includes a CCD chip.

7. The assembly as set forth in claim 1, wherein the light source is an LED light source.

8. The assembly as set forth in claim 1, wherein the light emitted by the light source:
   is unpolarized, and/or
   has a beam diameter of between 5 mm and 15 mm, and/or
   is collimated, and/or
   has a half-angle divergence of between 0.1° and 0.4°, and/or
   has a spectrum with a plurality of different wavelengths from a range of visible light.

9. The assembly as set forth in claim 8, wherein the beam diameter is 10 mm.

10. The assembly as set forth in claim 8, wherein the half-angle divergence is 0.25°.

11. The assembly as set forth in claim 1, wherein the assembly includes an evaluation unit for evaluation of the light pattern recorded by the camera.

12. The assembly as set forth in claim 1, wherein at least the light source, the holding device, the diffusing screen, the camera and the semi-transmitting optical element are arranged in an apparatus for suppressing background light.

13. A method of analyzing a light pattern caused by refraction and reflection at a precious stone by an assembly as set forth in claim 1, the method comprising:
   i. holding the precious stone to be analyzed in the holding device;
   ii. illuminating the precious stone by the light source; and
   iii. recording the light pattern imaged on the diffusing screen by the camera.

14. The method as set forth in claim 13, wherein steps ii. and iii. are repeated at least once with a differing illumination time and/or a differing intensity and/or a differing polarization.

15. The method as set forth in claim 13, further comprising:
   iv. evaluating the light pattern recorded by the camera by an evaluation unit.

16. The method as set forth in claim 15, wherein an HDR image is produced from at least two light patterns recorded with differing illumination times and/or differing intensities and/or differing polarizations.

17. The method as set forth in claim 15, wherein the light pattern recorded by the camera is compared to at least one light pattern stored in the evaluation unit.

18. The method as set forth in claim 17, wherein the at least one light pattern stored in the evaluation unit is a simulated light pattern.

19. The assembly as set forth in claim 1, wherein the semi-transmitting optical element is configured to deflect the light emitted by the light source in the direction of the precious stone such that a part of light incident on the precious stone passes into the precious stone, is refracted inside the precious stone and experiences total reflections at surfaces of the precious stone.

* * * * *